US00PP12258P2

(12) United States Plant Patent
Lenz

(10) Patent No.: US PP12,258 P2
(45) Date of Patent: Dec. 4, 2001

(54) *POTENTILLA FRUTICOSA* PLANT NAMED 'UMAN'

(75) Inventor: Louis M. Lenz, Winnipeg (CA)

(73) Assignee: University of Manitoba, Winnipeg (CA)

( * ) Notice: Subject to any disclaimer, the term of this patent is extended or adjusted under 35 U.S.C. 154(b) by 0 days.

(21) Appl. No.: 09/545,413

(22) Filed: Apr. 7, 2000

(51) Int. Cl.[7] ..... A01H 5/00
(52) U.S. Cl. ..... Plt./237
(58) Field of Search ..... Plt./237

*Primary Examiner*—Bruce R. Campell
*Assistant Examiner*—Kent L. Bell
(74) *Attorney, Agent, or Firm*—Burns, Doane, Swecker & Mathis, L.L.P.

(57) ABSTRACT

A new and distinct cultivar of Shrubby Potentilla botanically known as *Potentilla fruticosa* is provided. Attractive single bicolored blossoms are displayed from the summer until the time of frost. Such flowers are deep yellow in coloration with orange-red radiating outward from the center. The plant is small to medium-sized and displays a neat, dense, and compact growth habit. Medium green pinnately compound leaves are formed. The plant can be grown as attractive ornamentation in the landscape under a wide range of climatic conditions.

2 Drawing Sheets

SUMMARY OF THE INVENTION

Figure 1:
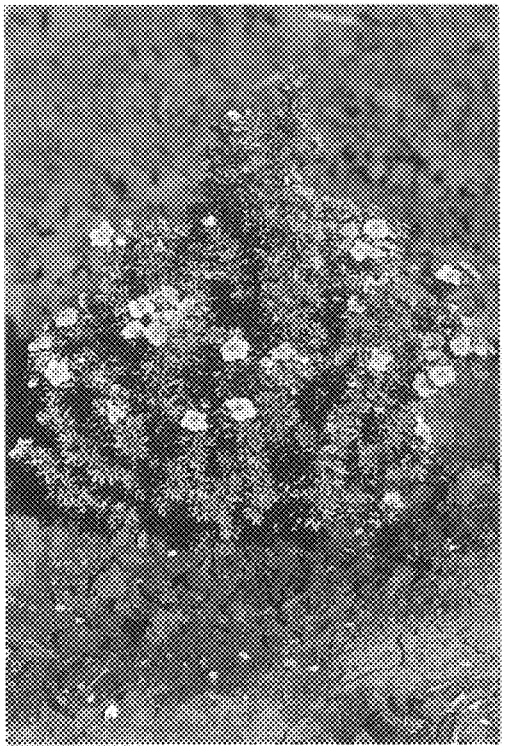

The present invention comprises a new and distinct cultivar of *Potentilla fruticosa* plant, and hereinafter is referred to by the cultivar name 'UMan'.

The new cultivar was the product of a planned breeding program which had the objective of creating a new *Potentilla fruticosa* cultivar having a novel and highly distinctive phenotype.

The breeding program which resulted in the creation of the new cultivar of the present invention was carried out during 1986 in a controlled environment at the Department of Plant Science, University of Manitoba, Winnipeg, Manitoba, Canada. Initially, the 'Pink Whisper' cultivar (non-patented in the United States) as pollen parent was crossed with the 'Yellowbird' cultivar (non-patented in the United States) as seed parent. The 'Pink Whisper' parent displayed medium-sized pink blossoms, and the 'Yellowbird' parent displayed medium-sized dark yellow semi-double blossoms. The parentage of the new cultivar can be summarized as follows:

'Yellowbird'×'Pink Whisper'.

The seedlings resulting from this cross were grown in test plots and a seedling was selected during 1987 in view of the outstanding horitcultural characteristics that are discussed hereafter. Had this selection not been made the new cultivar of the present invention would have been lost to mankind. This diploid seedling initially was designated Selection No. 87129. It was found that this new cultivar of the present invention exhibited the following combination of characteristics:

(a) is a small to medium sized plant having a dense and compact growth habit, (b) forms attractive medium green pinnately compound leaves, and (c) forms in profusion attractive single bicolored flowers that are deep yellow with orange-red coloration radiating outward from the center.

The new cultivar displays a dense, compact and neat appearance. It can be used to provide attractive ornamentation in the landscape under a wide range of climatic conditions. The flowers are formed from summer until frost in Manitoba, Canada. The flower coloration varies somewhat depending upon the temperature that is encountered. For instance, a more intense red is observed when grown under cooler weather conditions. Since the 'UMan' cultivar has not been observed under all possible environmental conditions to date, it is possible that the phenotype may vary somewhat with other variations in the environment.

The new cultivar of the present invention readily can be distinguished from the previously released 'Pink Beauty' cultivar (U.S. Plant Pat. No. 9,874). More specifically, the blossoms of the 'Pink Beauty' cultivar are semi-double and pink in coloration while those of the new 'UMan' cultivar are single and are bicolored deep yellow and orange-red.

Asexual propagation of the new cultivar by softwood cuttings at (a) the University of Manitoba, Winnipeg, Manitoba, Canada, (b) Portage la Prairie, Manitoba, Canada, and (c) St. Paul, Minn., U.S.A., has demonstrated that the characteristics of the new cultivar described herein are firmly fixed, are reproduced true to type, and are retained through successive generations of asexual propagation.

BRIEF DESCRIPTION OF THE PHOTOGRAPHS

The accompanying photographs show in color as nearly true as is reasonably possible to make the same in color illustrations of this character, plants, foliage, and blossoms of the new cultivar together with the blossoms and foliage two other *Potentilla fruticosa* cultivars for comparative purposes. The plants were approximately four years of age. The photographs were prepared during September at Portage la Prairie, Manitoba, Canada.

Figure 2:
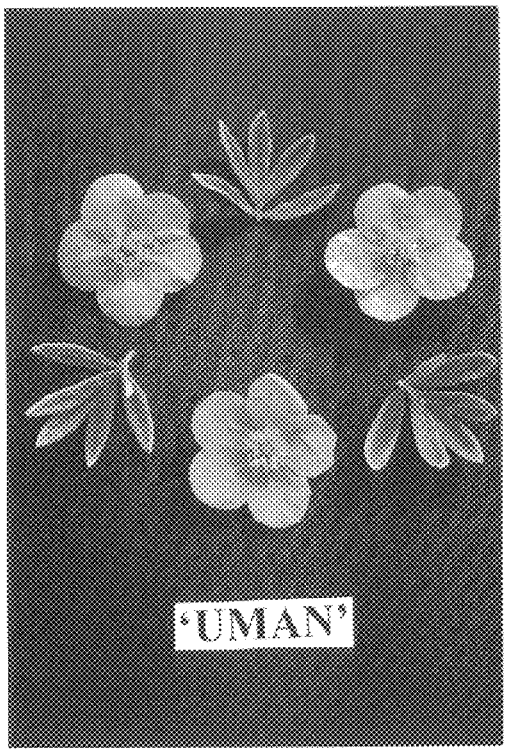
Figure 3:
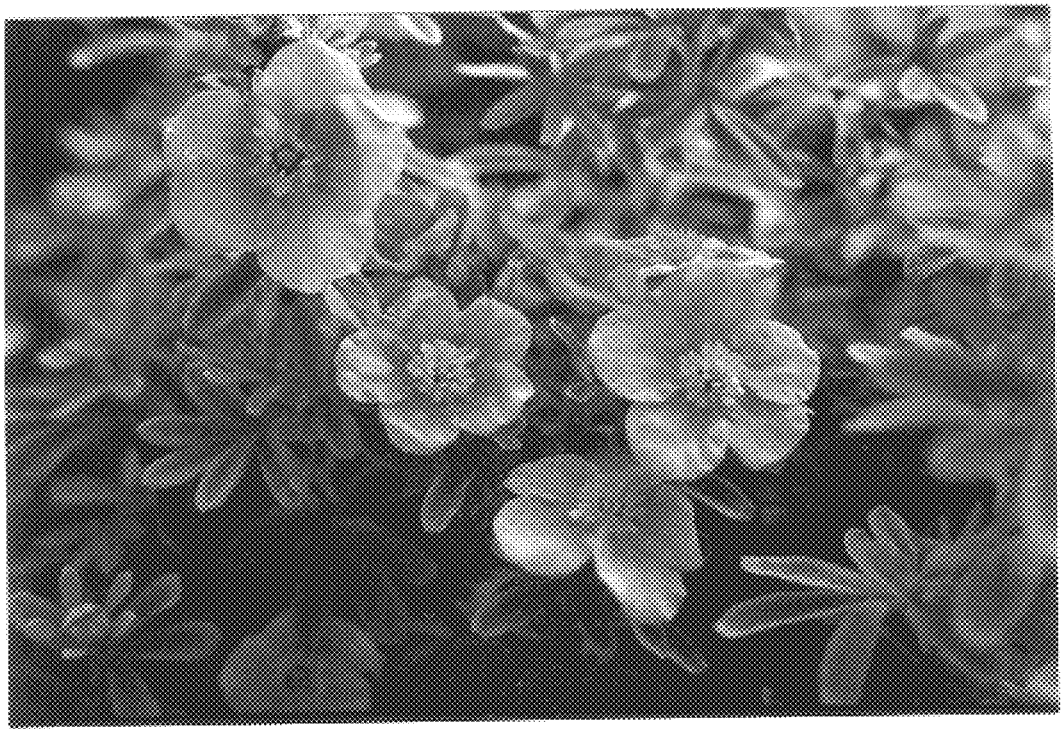
Figure 4:
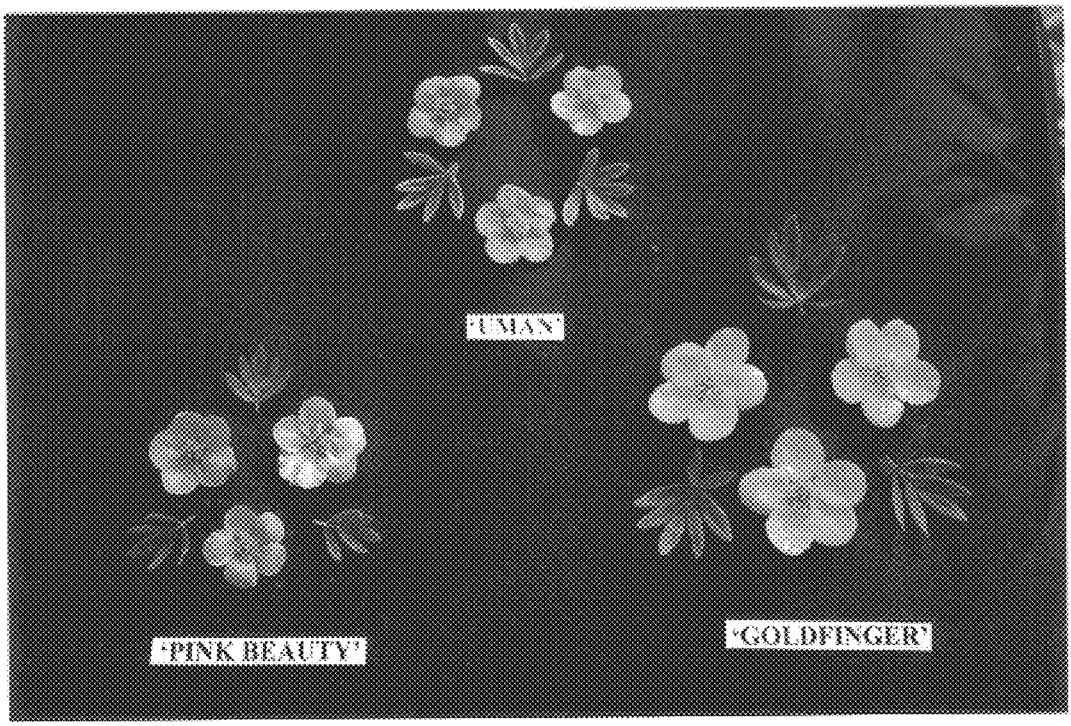

FIG. 1—illustrates a single flowering plant of the 'UMan' cultivar while growing in the landscape wherein the compact growth habit is illustrated;

FIG. 2—illustrates typical blossoms and foliage of the 'UMan' cultivar when removed from the plant;

FIG. 3—illustrates a close view of a portion of a typical flowering plant of the 'UMan' cultivar wherein the blossoms and foliage are shown; and FIG. 4—illustrates for comparative purposes typical blossoms and foliage of the new 'UMan' cultivar, the 'Pink Beauty' cultivar (U.S. Plant Pat. No. 9,874) and the 'Goldfinger' cultivar (non-patented in the United States) of *Potentilla fruticosa* when removed from the plant. The 'UMan' cultivar is shown at the top center, the 'Pink Beauty' cultivar at the lower left, and the 'Goldfinger' cultivar at the lower right.

DETAILED DESCRIPTION

The following description is based on the observation of a test planting of four year-old plants of the new 'UMan' cultivar at Portage la Prairie, Manitoba, Canada. Color terms are presented with reference to The R.H.S. Colour Chart of The Royal Horticultural Society, London, England. Such plants had been asexually reproduced by the use of cuttings. General terms are to be accorded their ordinary dictionary significance.

In the following Table, the new 'UMan' cultivar is compared using average dimensions to the 'Goldfinger' cultivar and the 'Pink Beauty' cultivar when plants of approximately the same age were grown at the same location under the same growing conditions.

| | 'UMan' | 'Goldfinger' | 'Pink Beauty' |
|---|---|---|---|
| Plant height (cm) | 57.1 | 81.4 | 64.2 |
| Plant width (cm) | 52.1 | 77.8 | 57.3 |
| Leaf length (cm) | 2.2 | 2.8 | 2.2 |
| Leaf width (cm) | 2.5 | 2.9 | 2.3 |
| Corolla: diameter (cm) | 3.0 | 3.5 | 2.6 |
| Corolla: petal width (cm) | 1.4 | 1.5 | 1.1 |
| Corolla: upper surface | Yellow Group 8A to 9A, Orange Group 26A to 28A | Yellow Group 9A to 12A | Red Group 54B to 54C and 56D |
| Corolla: under surface | Yellow Group 9A to 9C | Yellow Group 9B | Red Group 55D, White Group 155D |

The buds are found and are typically approximately 4 mm in size. The coloration is Green Group 141D at the base and is streaked with Red-Purple Group 60A.

The bicolored blossoms display shades of orange-red that radiate from center of the blossoms onto the base coloration of deep yellow (as illustrated). The intensity of the red coloration increases with cooler growing conditions.

The blossoms of the 'UMan' cultivar are medium-sized with respect to the corolla diameter and commonly last approximately 7 to 10 days on the plant. The flower is solitary (i.e., cymose). The flowering shoots are displayed in a dense profusion. The corolla under surface is Yellow Group 9C to 9D. The young stamens are Yellow-Green Group 153C and change to brown at late maturity. The stamens are approximately 2 mm in length. The calyx bract width tends to be narrower than the sepal width. The calyx bract length tends to be slightly longer than the sepal length.

The flower petals are five in number and substantially round (as illustrated in FIG. 2). Their diameter commonly is approximately 14 mm with both the apex and base being rounded. The petal margin is involuted.

The filaments typically number approximately 30 to 35, and are approximately 1 mm in length. The anthers are Yellow-Green Group 153C in coloration. The styles commonly number approximately 40 to 45, are approximately 0.75 mm in length. and are White Group 155A in coloration. The stigma is Yellow-Green Group 153D in coloration. The ovary is approximately 3 mm in diameter and Green Group 143C in coloration.

Pollen is formed in a sparse quantity and is Yellow Group 3B in coloration.

The calyx bracts are oblanceolate in configuration, approximately 9 mm in length, and approximately 3 mm in width. The apex is acute and the base is rounded. The margin configuration is smooth and revoluted. The coloration on the upper surface typically is Green Group 138A, and on the coloration of the under surface Green Group 138B.

The sepals are broad ovate in configuration, approximately 9 mm in length, and approximately 4 mm in width. The apex is acuminate the base is rounded. The margin configuration is smooth and revoluted. The coloration of the upper surface is Yellow-Green Group 154C and the coloration of the under surface is Yellow-Green Group 145A.

The leaves are pinnately compound and the leaflets are elliptic-oblong in configuration. The leaflets are five in number, sessile, have a revoluted margin (i.e., rolled towards the under side), and lack margin serration. The leaflets typically possess an acute apex and are grey-green when unfolding. When open, the leaflets typically are Green Group 138A on the upper surface and Green Group 138B on the under surface. Green leaflet coloration retained in the autumn. The petioles are approximately 4 mm in length, approximately 1 mm in diameter, and are Green Group 138B in coloration.

The stems possess a medium concentration of pubescence. When using a scale of 1 to 9 with 1 being the absence of pubescence and 9 being dense pubescence, the pubescence is 5 on the upper stem surface and 4 on the under stem surface. For three year-old container grown plants typical stem lengths are approximately 23 to 27 cm, typical stem diameters are approximately 2 to 3 mm, typical internode lengths are approximately 60 to 80 mm, and the stem coloration is Greyed-Orange Group 166A.

The branching is semi-upright and forms a dense, neat and compact overall growth habit. The plant size is small to medium in height and width. For instance, four-year old plants typically average approximately 57.1 cm in height and approximately 52.1 cm in width. A fully mature plant will reach a height of approximately 60 cm.

The new cultivar is hardy in U.S.D.A. Hardiness Zone No. 2, and can be utilized as a distinctive and colorful landscape planting.

The new cultivar, as other *Potentilla fruticosa* plants displays a high resistance to diseases and insects under field growing conditions. Spider mites may be a problem when grown in a greenhouse setting.

I claim:

1. A new and distinctive cultivar of *Potentilla fruticosa* plant having the following combination of characteristics:

(a) is a small to medium-sized plant having a dense and compact growth habit, (b) forms attractive medium green pinnately compound leaves, and (c) forms in profusion attractive single bicolored flowers that are deep yellow with orange-red coloration radiating outward from the center;

substantially as illustrated and described.

* * * * *